(12) United States Patent
Hooda et al.

(10) Patent No.: US 12,419,706 B2
(45) Date of Patent: *Sep. 23, 2025

(54) SURGICAL ARM AND METHOD OF PROVIDING VISUAL GUIDANCE FOR OPERATING SAME

(71) Applicant: Stryker European Operations Limited, Carrigtwohill (IE)

(72) Inventors: Ritesh Hooda, Rohtak (IN); Dinesh Sharma, Faridabad (IN); Dieter Teschke, Merdingen (DE); Hanna Anneser, Freiburg (DE); Udo Pfrengle, Vorstetten (DE); Ashley Nicodemus, San Jose, CA (US); Gina Giambalvo, Kalamazoo, MI (US); Amit Pandita, Gurgaon (IN); Matthias Wapler, Kirchzarten (DE)

(73) Assignee: Stryker European Operations Limited, Carrigtwohill (IE)

( * ) Notice: Subject to any disclaimer, the term of this patent is extended or adjusted under 35 U.S.C. 154(b) by 212 days.

This patent is subject to a terminal disclaimer.

(21) Appl. No.: 18/107,713

(22) Filed: Feb. 9, 2023

(65) Prior Publication Data

US 2023/0181270 A1    Jun. 15, 2023

Related U.S. Application Data

(63) Continuation of application No. 16/739,786, filed on Jan. 10, 2020, now Pat. No. 11,602,400.

(51) Int. Cl.
*A61B 34/30* (2016.01)
*A61B 34/20* (2016.01)

(52) U.S. Cl.
CPC .............. *A61B 34/30* (2016.02); *A61B 34/20* (2016.02); *A61B 2034/2055* (2016.02)

(58) Field of Classification Search
CPC . A61B 34/30; A61B 34/20; A61B 2034/2055; A61B 90/50; A61B 34/70; A61B 2034/303; A61B 90/94; A61B 90/92; A61B 2090/3983
See application file for complete search history.

(56) References Cited

U.S. PATENT DOCUMENTS

| | | |
|---|---|---|
| 7,670,345 B2 | 3/2010 | Plassky et al. |
| 2008/0306375 A1 | 12/2008 | Sayler et al. |
| 2009/0171184 A1 | 7/2009 | Jenkins et al. |
| 2021/0212778 A1 | 7/2021 | Hooda et al. |

FOREIGN PATENT DOCUMENTS

| | | |
|---|---|---|
| EP | 1430842 A1 | 6/2004 |
| WO | 2018103945 A1 | 6/2018 |

*Primary Examiner* — Thomas McEvoy
(74) *Attorney, Agent, or Firm* — Howard & Howard Attorneys PLLC

(57) ABSTRACT

A surgical arm is presented. The surgical arm comprises a first interface configured to receive a device for performing or assisting a surgical procedure and multiple adjustment members configured to adjust the surgical arm relative to a respective adjustment axis. The surgical arm further comprises at least two operating members configured to operate different ones of the adjustment members, wherein the operating members are marked with different visual codings. Further a method for providing visual guidance for operating the surgical arm according to a pre-determined surgical approach is presented.

20 Claims, 7 Drawing Sheets

SURGICAL ARM AND METHOD OF PROVIDING VISUAL GUIDANCE FOR OPERATING SAME

CROSS REFERENCE TO RELATED APPLICATIONS

This is a continuation application of copending U.S. application Ser. No. 16/739,786, filed Jan. 10, 2020, the entire contents of which are hereby incorporated by reference.

TECHNICAL FIELD

The present disclosure relates to assisted surgery. In particular, a surgical arm adjustable relative to multiple adjustment axes is presented. Also presented is a method of providing visual guidance for operating the surgical arm. The present disclosure can be implemented as a surgical arm, a method, a computer program product and a system.

BACKGROUND

Computer assisted surgery has made considerable progress in recent years, for example to plan and visualize a surgical approach for a surgeon to reach a surgical target inside a patient's body. To assist the surgeon in properly operating a surgical tool, such as a drill or a biopsy needle, in accordance with the planned surgical approach, a surgical arm may be used. The surgical arm is adjustable relative to multiple adjustment axes and, once properly adjusted in accordance with the planned surgical approach, permits an exact guidance of the surgical tool to the surgical target.

It will be appreciated that a proper adjustment of the surgical arm is of utmost importance for an optimal surgical result. At the same time, the adjustment has to be performed as quickly as possible to shorten the duration of the surgical procedure and the resulting stress on the patient.

SUMMARY

There is a need for a surgical arm that can be adjusted quickly and in an exact manner. Also, there is a need for providing visual guidance for efficiently operating such a surgical arm.

According to one aspect, a surgical arm is presented, the surgical arm comprising a first interface configured to receive a device for performing or assisting a surgical procedure and also comprising multiple adjustment members configured to adjust the surgical arm relative to a respective adjustment axis. The surgical arm further comprises at least two operating members configured to operate different ones of the adjustment members, wherein the operating members are marked with different visual codings.

The surgical arm may be a mechanical element configured to be used during a surgical procedure (e.g., in a sterile operating room). The surgical arm may be used by a surgeon for placing and/or aligning a surgical tool or any other device (e.g., a guidance member for the surgical tool). In one example, the surgical arm may be used for properly orienting a biopsy needle or other surgical tool. As such, the first interface may be configured to receive a guidance device such as a needle sleeve shaped to receive the biopsy needle, or such as a drill sleeve.

The adjustment members may be mechanical components, for example gearwheels, toothed racks or (ball) joints. The adjustment members may be configured to move at least one moveable part of the surgical arm along and/or around a specific axis.

Each particular adjustment axis may be a rotational or a translational axis. In case of a rotational adjustment axis, the surgical arm may be configured to be moved around this axis. In case of a translational axis, the surgical arm may be configured to be moved along this axis. For example, the surgical arm may comprise two rotational adjustment axes and two translational adjustment axes. In another example, the surgical arm may only comprise one rotational adjustment axis and one translational adjustment axis. The respective rotational and translational adjustment axes may be perpendicular to one another.

The operating members may be manually or electrically (e.g., by an electric motor) operable. Each of the operating members may be configured such that by operating the operating member, the surgical arm will be moved around a specific rotational adjustment axis or along a specific translational adjustment axis associated with the operating member. In one example, one or more of the operating members may be rotatable elements, such that rotating the operating members in a first rotation direction causes the surgical arm to be moved in a first adjustment direction relative to a specific adjustment axis associated with the operating member. When rotating the operating member in a second rotation direction different from (e.g., opposite to) the first rotation direction, the surgical arm may be moved in a second adjustment direction different from (e.g., opposite to) the first adjustment direction relative to the specific adjustment axis. In other examples, the operating members may be slidable elements (e.g., levers) or pushable elements (e.g., buttons).

The visual codings may be cognitively detectable by a human observer (e.g., a user such as a surgeon) and/or electrically detectable by an electronic component (e.g., a camera of a surgical navigation system). Different visual codings may be clearly distinguishable from one another by the human observer as well as the electronic component. In one example, the visual codings may be different colors. In another example, the visual codings may be different visual patterns, e.g., different geometric forms. In yet another example, the visual codings may be different shadings, e.g., dashed and/or dotted lines.

The surgical arm may further comprise at least two locking members associated with different ones of the operating members. The locking members may be manually or electrically (e.g., by an electric motor) operable. Each of the locking members may be configured to lock the arm in position with respect to a specific movement relative to the respective adjustment axis of the associated operating member. Like the operating members, the locking members may also be rotational, slidable and/or pushable elements. When one of the locking members is operated to be active (i.e., locking), the surgical arm may no longer be adjustable relative to the specific adjustment axis of the associated operating member. In other words, in a locked state, the locking member may fix the surgical arm with respect to a specific movement (e.g., rotatory or translatory) relative to a specific alignment axis.

In some variants, the locking members may respectively be coded with the same visual coding as the operating member associated with the respective adjustment axis. The respective visual codings of a locking member and an associated operating member may be identical. For example, if a specific operating member associated with a respective adjustment axis is encoded with a blue color, the locking member associated with the specific operating member may also be encoded with a blue color. In another example, if a specific operating member is encoded with a dotted pattern, the locking member associated with said operating member may also be encoded with the dotted pattern.

In some implementations, the operating members as well as the locking members may be configured rotatably. As described above, rotating the operating member in a first rotation direction may cause the surgical arm to be adjusted in a first adjustment direction. Likewise, rotating the locking member in a first direction may fix an alignment of the surgical arm relative to a specific alignment axis. Additionally, rotating the locking member in a second direction different from the first direction may enable further alignment of the surgical arm relative to the specific alignment axis. The operating members and the locking members may for example be represented by rotatable turning knobs or pivotably mounted levers.

At least a first one of the adjustment members may be configured to adjust the surgical arm along a translational adjustment axis. At least a second one of the adjustment members may be configured to adjust the surgical arm around a rotational adjustment axis. In one variant, a specific adjustment member may be associated with a specific adjustment axis. Alternatively, two or more adjustment members may be associated with the same adjustment axis. In the latter variant, a first adjustment member may be configured to adjust the surgical arm in one direction (e.g., a positive x-direction) and a second adjustment member may be configured to adjust the surgical arm in a second direction (e.g., a negative x-direction).

In some variants, the surgical arm may comprise a second interface for receiving a tracking device configured to be tracked by a surgical navigation system. The tracking device may for example be an optical tracking device such as a reflective marker. Additionally, or in the alternative, the surgical arm may comprise the tracking device configured to be tracked by a surgical navigation system.

As said, the different visual codings may be different colors. One operating member and the locking members associated with that operating member may be encoded in yellow, and a different operating member associated with a different locking member may be encoded in blue.

In some embodiments, the surgical arm may further comprise a guidance device coupled to the first interface. The guidance device may define an operative axis and may be configured to guide a surgical tool along the operative axis. The guidance device may be configured to be received by (e.g., to be coupled to) the first interface.

According to a second aspect, a method of providing visual guidance for operating a surgical arm according to a pre-determined surgical approach is provided. The surgical arm comprises a first interface configured to receive a device for performing or assisting a surgical procedure and multiple adjustment members configured to adjust the surgical arm relative to a respective adjustment axis. The surgical arm further comprises at least two operating members configured to operate different ones of the adjustment members, wherein the operating members are marked with different visual codings. The method comprises the steps of determining at least one of a current position and a current orientation of the first interface or a device received by the first interface, and determining, based on the pre-determined surgical approach, at least one of a target position and a target orientation of the interface or the device. The method further comprises the step of, based on a difference between at least one of the current and target positions and the current and target orientations, determining that an adjustment of the surgical arm is required relative to at least one adjustment axis; and triggering a display of the visual coding associated with the at least one operating member associated with the at least one adjustment axis so as to provide visual guidance.

The steps may be performed by a processing unit of a computer system (e.g., as part of a surgical navigation system). The processing unit may trigger a display unit (e.g., a monitor) of the computer system to provide the visual guidance.

The pre-determined surgical approach may be a planned trajectory of a surgical tool for reaching an area within a patient's body where a surgical procedure is to be performed. For example, the pre-determined surgical approach may correspond to the planned trajectory of a biopsy needle that is to be entered into the skull of a patient. The pre-determined surgical approach may be pre-operatively planned using a computer system, such as a surgical navigation system.

The planned trajectory may comprise a starting point (e.g., an entry point into the body) according to the pre-determined surgical approach. Alternatively or additionally, the planned trajectory may comprise an endpoint (e.g., an anatomical target) according to the pre-determined surgical approach.

In some variants, the visual guidance may comprise a display of the visual coding in combination with an indication of a direction in which the associated operating member is to be operated. For example, if the visual codings are different colors and the operating members are configured rotatably, visual guidance may be provided by displaying a color coding of a specific operating member together with the image of an arrow depicting a direction in which the rotatable operating member is to be rotated.

The visual guidance may further comprise a display of the visual coding in combination with an indication of an amount by which the associated operating member is to be operated. The indication of an amount by which the associated operating member is to be operated may be in the form of a first number of geometric elements (and/or a first geometric form such as a circle having a first size) in association with the visual coding of the operating member. For example, the operating members may be rotatably mounted and the indication could be represented by a number of segments of a circle representative of a number of degrees by which a specific operating member has to be turned.

The method may further comprise displaying a second number of geometric elements (and/or a second geometric form such as a circle having a second size different form the first size) in association with a visual coding different than the visual coding of the first number of geometric elements (and/or the first geometric form), the second number of geometric elements (or the second geometric form) being indicative of an amount by which the associated operating member has been operated. In the above described example, a first number of segments of a circle may be filled with a visual coding associated with the respective operating member and a second number of segments of the circle may be filled with a visual coding different from the visual coding associated with the respective operating member.

In some variants, the method may further comprise determining a specific adjustment axis relative to which the surgical arm deviates the most among all adjustment axes from the pre-determined surgical approach. In this case the method may further comprise prioritising the provision of visual guidance for said specific adjustment axis over any other adjustment axis.

The method may further comprise the step of trigger a display of a numerical value indicative of an amount by which a specific adjustment axis deviates from the pre-determined surgical approach. The method may further comprise triggering a display of a superposition of at least one of the current position and the current orientation of the first interface or a device received in the first interface relative to the pre-determined surgical approach.

In some implementations, the at least one of a current position and a current orientation of the first interface or the device received by the first interface may be determined by tracking, using a surgical navigation system, a tracking device that is in a fixed spatial relationship with at least one of the first interface and the device received by the first interface.

According to a further aspect, a computer program product is presented, the computer program product comprising computer program instructions to perform the method steps of the above described method when executed by a processor.

According to a further aspect, a system comprising the surgical arm as described above and the above described computer program product is presented.

BRIEF DESCRIPTION OF THE DRAWINGS

Further details, advantages and aspects of the present disclosure will become apparent from the following embodiments taken in conjunction with the drawings, wherein.

DETAILED DESCRIPTION

Figure 1:
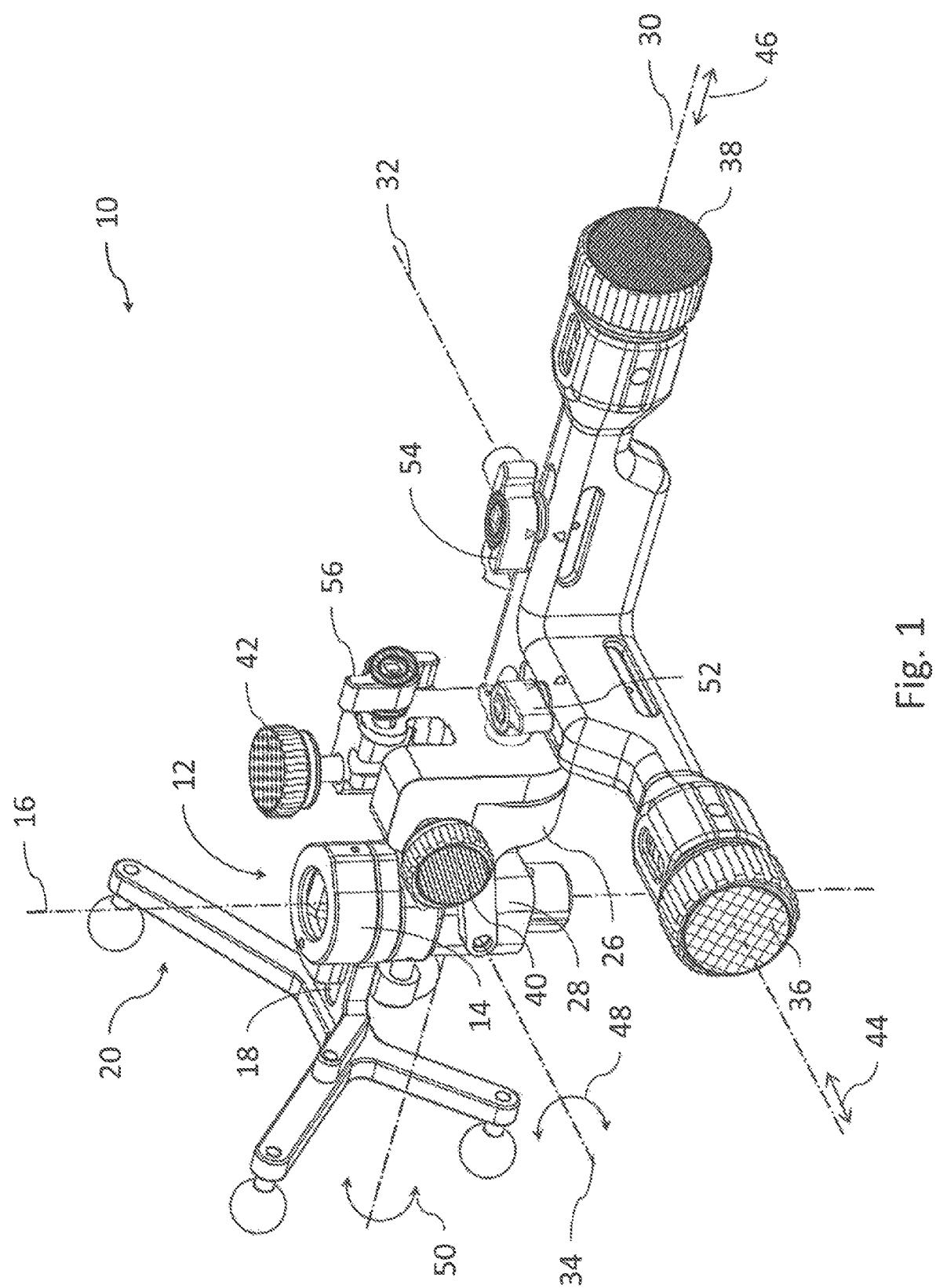
FIG. 1 shows a perspective view of an embodiment of a surgical arm.

In the following description, exemplary embodiments of a surgical arm and a technique of providing visual guidance for operating the surgical arm will be explained with reference to the drawings. The same reference numerals will be used to denote the same structural features.

Figure 2A:
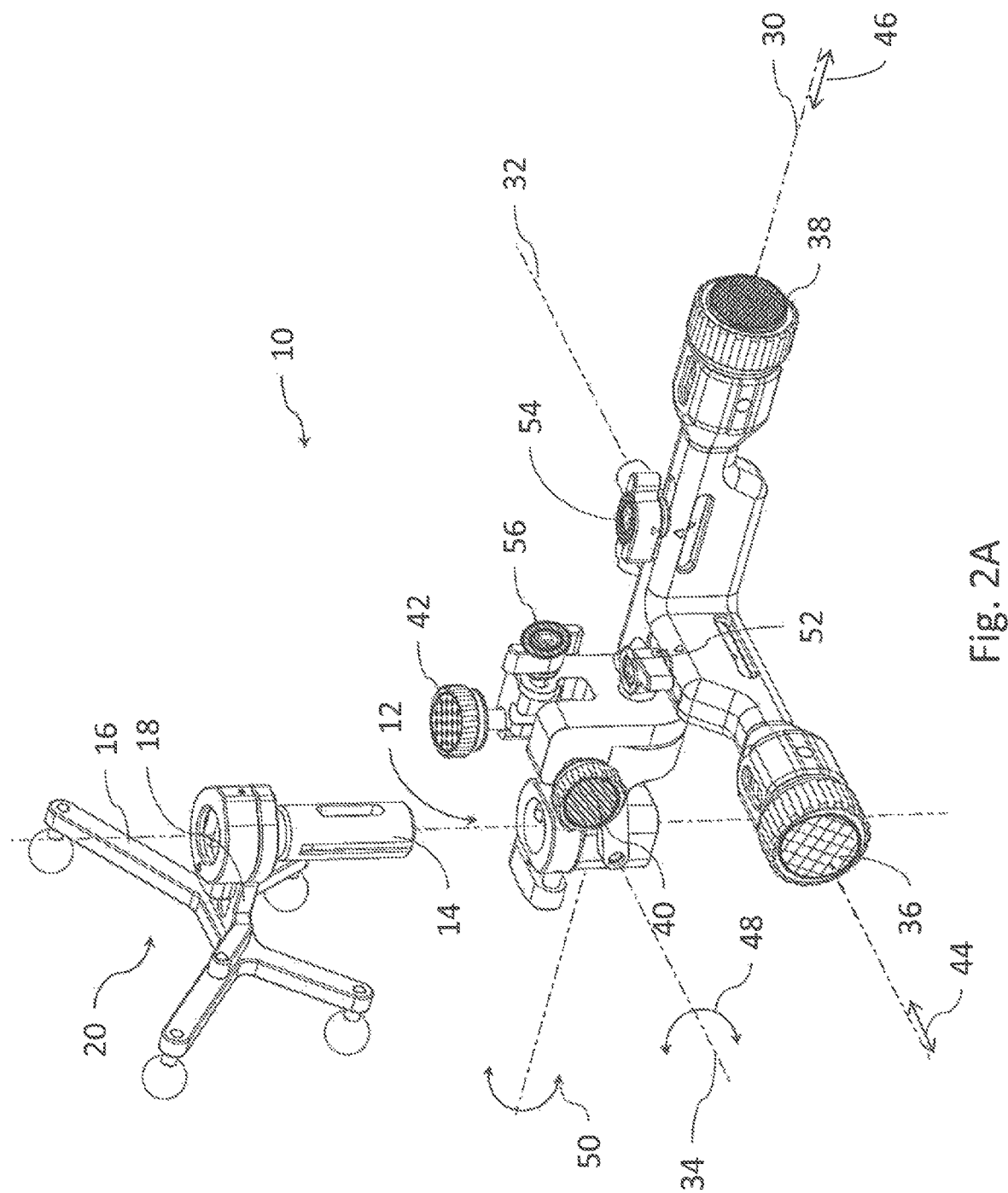
FIG. 2A shows a perspective view of the surgical arm of FIG. 1, wherein a guidance device with an attached tracking device has been removed from the surgical arm.
Figure 2B:
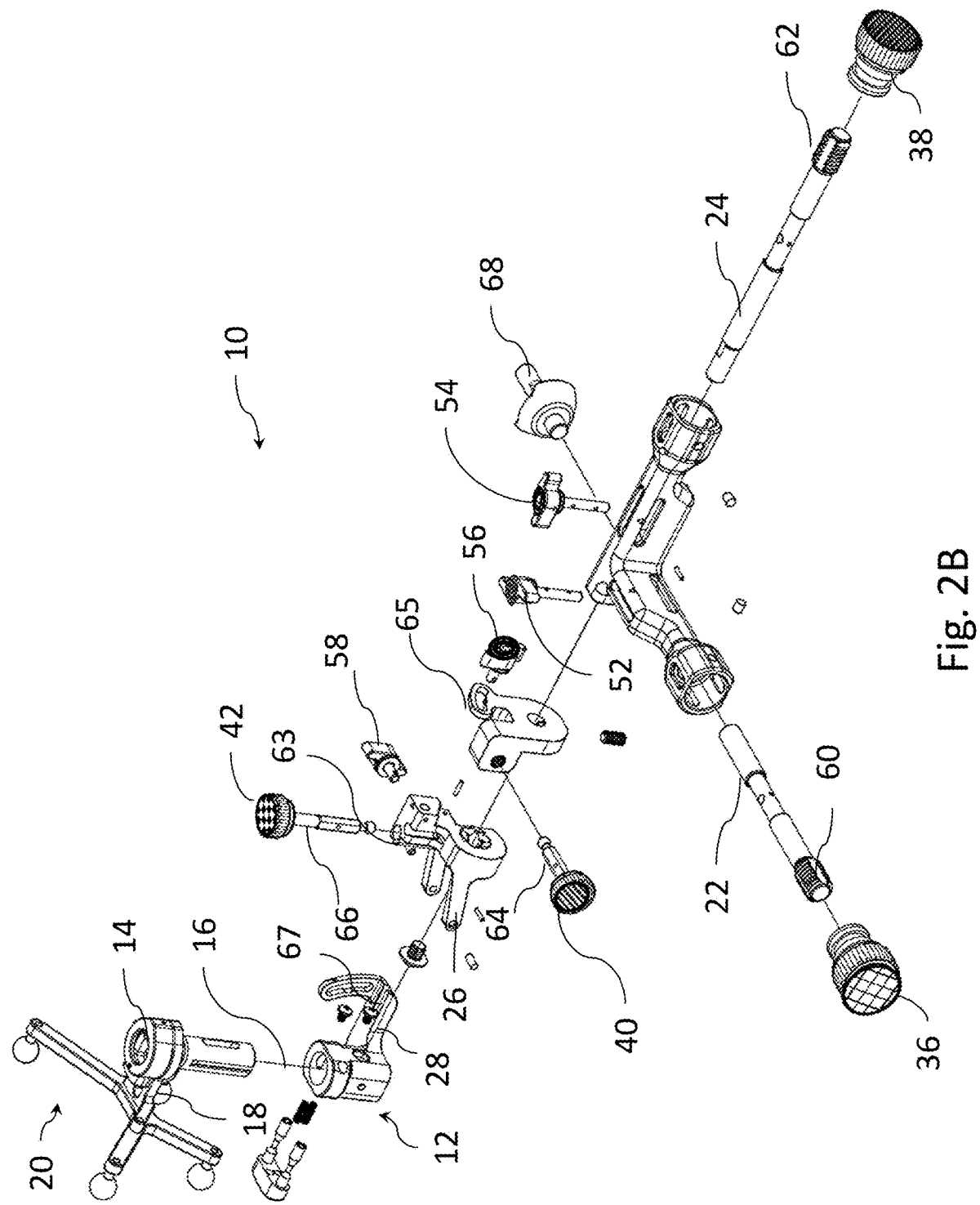
FIG. 2B shows an exploded view of the surgical arm of FIG. 2A.

FIGS. 1, 2A and 2B show an embodiment of a surgical arm 10 that is configured to be used during a surgical procedure. The surgical arm 10 is intended to be attached to a support frame (not shown) that is fixedly positioned in an operating room relative to a patient. As an example, the surgical arm 10 may be attached via the support frame to an operating table or an operating chair. In some variants, the surgical arm 10 is used for computer-assisted neuro-surgery, for example to guide a surgical tool towards a surgical target (e.g., a tumor) within the patient's skull.

The surgical arm 10 comprises an interface 12 configured to receive a device for performing or assisting the surgical procedure. In the present embodiment, the device interface 12 is configured as a sleeve with a cylindrical through-hole. It will be apparent to one skilled in the art that the device interface 12 could also be configured in a different manner, for example as a rail.

The device to be received by the device interface 12 can be a surgical tool or can be configured to cooperate with (e.g., to guide) a surgical tool. In the exemplary embodiment of FIGS. 1, 2A and 2B, the device interface 12 is configured to receive a guidance device 14 for a biopsy needle, a surgical drill or other any surgical tool. The guidance device 14 is concentrically received within the sleeve-like device interface 12 and defines an operative axis 16. In the present embodiment, the guidance device 14 has a cylindrical through-hole configured to guide the surgical tool along the operative axis 16 towards the surgical target within the patient. It will be appreciated that in other embodiments, the guidance device 14 could be realized as a guide rail or otherwise.

The arm 10 comprises a further interface 18 configured to receive a tracking device 20 that is to be tracked by a surgical navigation system. In the present embodiment, the tracking device 20 is an optical tracking device and comprises four reflective spheres that are located spaced apart from each other at the end of four respective arms. Of course, the tracking device 20 could also be configured to comprise active light sources or other trackable elements. Moreover, the tracking device 18 could also be integrally formed with a component of the surgical arm 10, such as the guidance device 14 or the device interface 12.

In the present embodiment, the tracker interface 18 is part of the guidance device 14, which in turn is detachably mounted in the device interface 12 (see FIGS. 1 and 2A). In other embodiments, the tracker interface 18 is mounted to the device interface 12 or another component of the surgical arm 10 with a fixed relationship to the device interface 12.

As shown in the exploded view of FIG. 2B, the surgical arm 10 comprises four adjustment members 22, 24, 26 and 28 configured to adjust the surgical arm 10 relative to different adjustment axes 30, 32 and 34. The adjustment members 22, 24, 26 and 28 are operated by operating members 36, 38, 40 and 42. In the present embodiment, the operating members 36, 38, 40 and 42 are configured rotatably, i.e., as turning knobs. However, the present disclosure is not limited thereto. For example, one or more of the operating members 36, 38, 40 and 42 could also be configured for translatory movement (e.g., as slidable and/or pushable elements). Moreover, one or more of the operating members 36, 38, 40 and 42 could be configured to be electrically operable by an electric motor (not shown).

In the present embodiment, each of the operating members 36, 38, 40 and 42 is configured to operate exactly one of the adjustment members 22, 24, 26 and 28. Operating one or more of the operating members 36, 38, 40 and 42 serves to adjust the surgical arm 10 relative to at least one adjustment axis 30, 32 and 34. More specifically, as illustrated in FIG. 1, operating the operating member 36 translatorily moves the surgical arm 10 along adjustment axis 32 in two opposite directions according to double-headed arrow 44. Likewise, operating the operating member 38 translatorily moves the surgical arm 10 along adjustment axis 30 in two opposite directions according to double headed arrow 46. The two adjustment axes 30, 32 extend perpendicular to each other.

On the other hand, operating member 40 is configured to rotationally move the surgical arm 10 around adjustment axis 30 in two opposite directions according to double headed arrow 48. Further, operating member 42 is configured to rotationally move the surgical arm 10 around adjustment axis 34 in two opposite directions according to double headed arrow 50.

As is clear from the above description, operating member 38 and operating member 40 are configured to adjust the surgical arm 10 relative to adjustment axis 30 in a translatory and in a rotary manner, respectively. Adjustment member 24 is configured to adjust the surgical arm 10 along adjustment axis 30 and adjustment member 26 is configured to adjust the surgical arm 10 around adjustment axis 30. In an alternative embodiment, adjustment axis 32 and adjustment axis 34 may coincide. In this or another embodiment, operating member 38 and operating member 42 may be configured to adjust the surgical arm 10 relative to different adjustment axes.

Each of the operating members 36, 38, 40 and 42 is marked with a different visual coding. The different visual codings can easily be distinguished by a human operator of the surgical arm 10 without significant cognitive effort.

In the drawings, each of the operating members 36, 38, 40 and 42 is exemplarily marked with a different geometric pattern. In particular, operating member 36 is marked with a pattern in the form of a grid. Further, operating member 38 is marked with a pattern in the form of dots. Operating member 40 is marked with a pattern in the form of straight lines. Operating member 42 is marked with a pattern in the form of black and white diamonds. It is to be understood that the visual codings in the form of geometric patterns of the operating members 36, 38, 40 and 42 only serve as an illustrative example and are not limited thereto. In another example, the operating members 36, 38, 40 and 42 may be marked with visual codings in the form of different colors (e.g., red, green, yellow and blue, respectively).

The surgical arm 10 depicted in FIGS. 1, 2A and 2B further comprises locking members 52, 54, 56 and 58. Locking member 58 is not visible in FIG. 1, but is shown in FIG. 2B. Each of the locking members 52, 54, 56 and 58 is associated with exactly one of the operating members 36, 38, 40 and 42. That is, locking member 52 is associated with operating member 36, locking member 54 is associated with operating member 38, locking member 56 is associated with operating member 40 and locking member 58 is associated with operating member 42. The association between the locking members 52, 54, 56 and 58 and the respective operating members 36, 38, 40 and 42 is depicted in the drawings by the fact that each of the locking members 52, 54 and 56 is marked with the same visual coding (i.e., the same geometric pattern) as its associated operating member 36, 38, 40 and 42. In more detail, locking member 52 is marked with the grid pattern of operating member 36, locking member 54 is marked with the dot pattern of operating member 38, locking member 56 is marked with the line pattern of operating member 40 and locking member 58 is marked with the black and white diamond pattern of operating member 42. Reference is made to the respectively marked rings encircling the locking symbols of the locking members 52, 54 and 56 in FIGS. 1 to 3B. The visual codings of the operating members 36, 38, 40 and 42 and the respective locking members 52, 54, 56 and 58 will be described in more detail with reference to FIGS. 3A and 3B below.

The locking members 52, 54, 56 and 58 are configured to lock the surgical arm 10 in position relative to a dedicated movement relative to the respective adjustment axis 30, 32, 34 of an associated operating member 36, 38, 40 and 42. That is, after the surgical arm 10 has properly been aligned relative to the patient with respect to each one of the adjustment axes 30, 32 and 34 using the operating members 36, 38, 40 and 42, the associated locking member 52, 54, 56 and 58 is operated such that the corresponding alignment of the surgical arm 10 can no longer be changed.

In the embodiment of FIG. 1, the locking members 52, 54, 56 and 58 are configured rotatably, i.e., in the form of rotatable levers. The locking members 52, 54, 56 and 58 may have a definite locking position. For example, rotating the locking members 52, 54, 56 and 58 clockwise by 90° may lock the surgical arm 10 in position relative to a dedicated movement with respect to the associated adjustment axis 30, 32 or 34 associated with the respective locking member 52, 54, 56 and 58. Further, rotating any of the locking members 52, 54, 56 and 58 counterclockwise by 90° may unlock the position of the surgical arm 10, i.e., the surgical arm may again be moveable relative to the associated adjustment axis 30, 32 and 34.

FIG. 2A shows the surgical arm 10 according to FIG. 1 in a partly disassembled configuration. In more detail, the guidance device 14 is removed from the device interface 12. As shown in FIG. 2A, the tracker interface 18 for detachably receiving the tracking device 20 is attached to the guidance device 14. As stated above, the surgical arm 10 can be operated with a variety of different surgical tools (e.g., a biopsy needle or a surgical drill). Depending on the specific surgical tool, a different guidance device 14, configured to receive the surgical tool, may have to be inserted into the first interface 12. As the tracker interface 18 is attached to the guidance device 14, a positional relationship between the tracking device 20 and the guidance device 14 can remain fixed and can be defined in advance, which simplifies the tracking process of for example a spatial orientation of the guidance device 14 (and, thus, of any surgical tool guided therein).

FIG. 2B shows an exploded view of the surgical arm 10 of FIG. 1. The four adjustment members 22, 24, 26 and 28 are clearly visible.

As can be seen in FIG. 2B, the adjustment members 22 and 24 comprise screw threads 60, 62 configured to adjust the surgical arm 10 upon rotation of the adjustment members 22 and 24 (via the associated operating member 36, 38) in a translational manner along the associated adjustment axis 30, 32 (not depicted in FIG. 2B). Further, the adjustment member 26 comprises a groove 63 accommodating a spherical front end of a shaft 64 of the operating member 40. The shaft 64 comprises a thread cooperating with a complementary thread in a bore of a stationary member 65. By turning the operating member 40, the shaft 64 moves towards or away from adjustment member 26 that is tiltable relative to the adjustment axis 30. As the spherical head of the shaft 64 is movably captured within the groove 63 of the adjustment member 26, a movement of the shaft 64 towards or away from the adjustment member 26 tilts, or rotates, the latter relative to adjustment axis 30.

In a similar manner as operating member 40, also operating member 42 comprises a threaded shaft 66 with a spherical head. The thread of shaft 66 cooperates with a complementary thread in a bore of adjustment member 26.

By turning operating member 42, shaft 66 moves towards or away from adjustment member 28 that is tiltable relative to the adjustment axis 34 (not depicted in FIG. 2B). As the spherical head of the shaft 66 is captured within a groove 67 of the adjustment member 28, a movement of the shaft 66 relative to the adjustment member 28 tilts, or rotates, the latter relative to the adjustment axis 34.

As can also be gathered from FIG. 2B, the surgical arm 10 further comprises an attachment interface 68 configured to attach the surgical arm 10 to a support frame (not shown). The support frame, in turn, may be attached to an operating table or an operating chair.

Figure 3A:
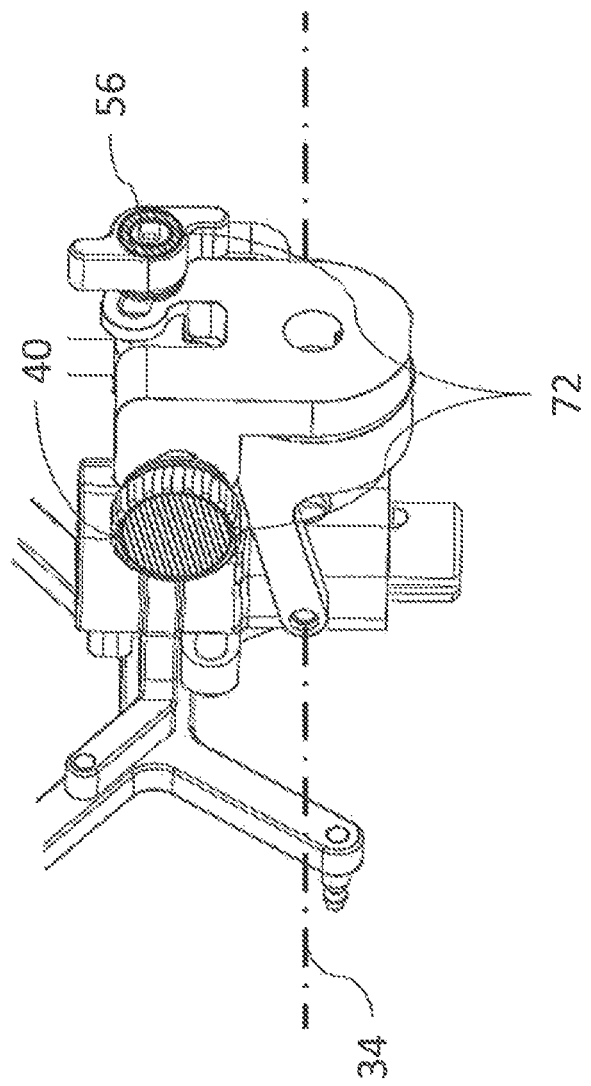
FIGS. 3A-3B illustrate enlarged views of different portions of the surgical arm of FIG. 1.
Figure 3B:
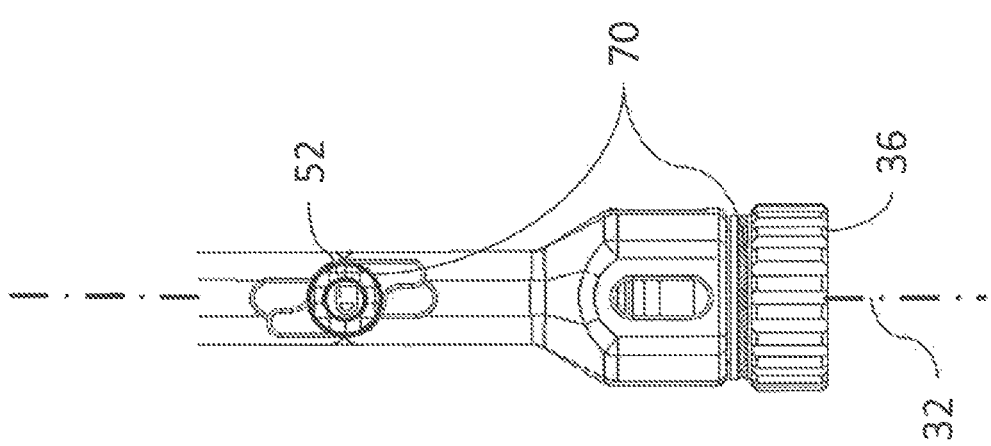

FIG. 3A shows a top view of a portion of the surgical arm 10, comprising the operating member 36 and the locking member 52 associated therewith. FIG. 3B, on the other hand, shows a front portion of the surgical arm 10, comprising the operating member 40 and the locking member 56 associated therewith. As can be seen in FIGS. 3A and 3B, each of the locking members 52, 56 is marked with the same visual codings as its associated operating member 36, 40. In particular, locking member 52 is marked with the same grid pattern 70 as its associated operating member 36. Further, locking member 56 is marked with the same line pattern 72 as its associated operating member 40. Therefore, it is immediately apparent to the user (e.g., a surgeon) that operating member 36 and locking member 52 pertain to the same adjustment axis 32. The same holds true for operating member 40 and locking member 56.

Furthermore, the different visual codings of the operating members and the associated locking members are also detectable by a camera, such as a camera of a surgical navigation system (e.g., the same camera that is also used to track the tracking device 20). Thus, also a processing unit of the surgical navigation system can determine each association between one of the visually coded operating members and one of the visually coded locking members. Moreover, an association between each visually coded operating member and the respective adjustment axis associated therewith can be known to the processing unit a priori (e.g., can be pre-stored in a storage medium). Consequently, the surgical navigation system can easily determine which operating member to operate in order to adjust the surgical arm 10 relative to a specific adjustment axis. Further, the surgical navigation system can determine which locking member to operate in order to lock the surgical arm 10 in position relative to a respective adjustment axis. The surgical navigation system may also be able to display said associations to a user in order to provide visual guidance for aligning the surgical arm 10, or to perform the alignment automatically (e.g., via electric motors).

The interaction between the user, such as the surgeon, and the surgical navigation system in order to provide visual guidance for operating the surgical arm 10 is now described in further detail with reference to FIGS. 4, 5 and 6A to 6D.

Figure 4:
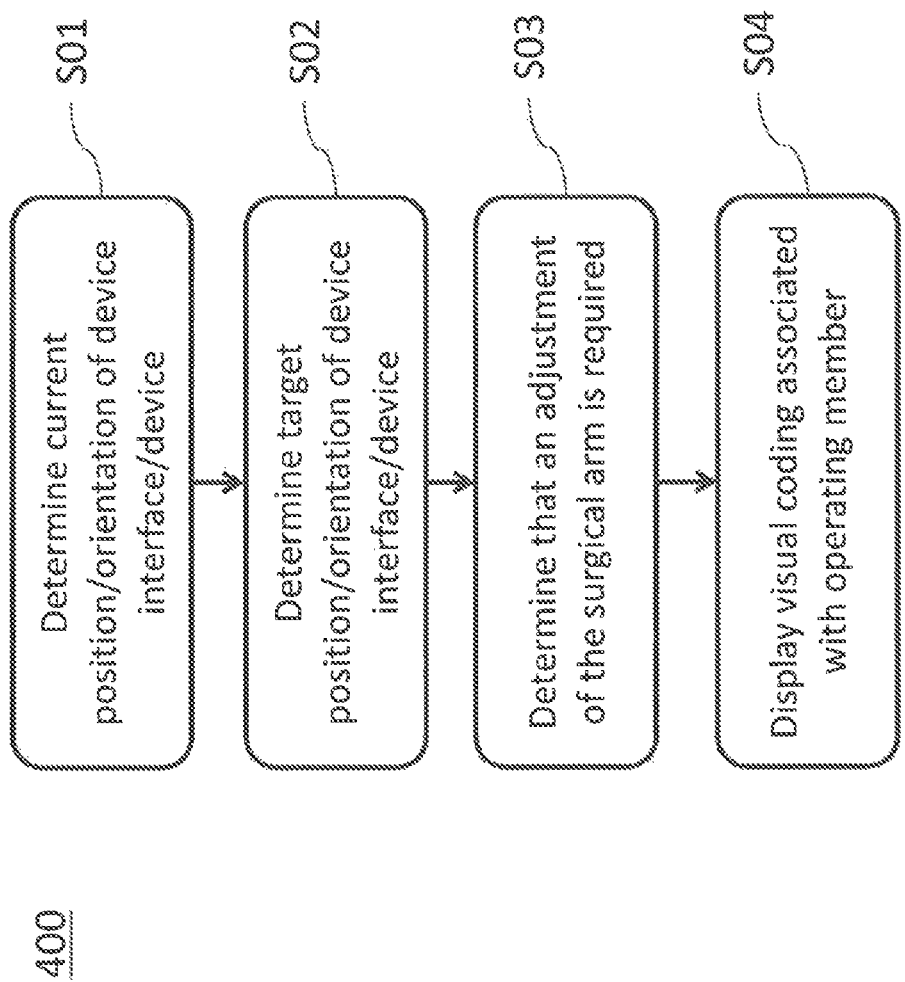
FIG. 4 shows a flow diagram of a method embodiment of providing visual guidance for operating a surgical arm according to a pre-determined surgical approach.

FIG. 4 shows a flow diagram 400 of an exemplary method of providing visual guidance for operating a surgical arm (e.g., the surgical arm 10) according to a pre-determined surgical approach.

The pre-determined surgical approach may be defined by at least one of a surgical target (e.g., in the form of a point or an extended object such as a tumor) located within a patient's body and an entry point where a surgical tool will enter the patient's body. In some variants, the surgical approach is defined by a trajectory that connects a planned (or actual) entry point at a body surface of the patient with a planned target. The pre-determined surgical approach may be defined by the surgeon pre-operatively using a computer system and previously generated patient images.

The method starts in step S01 with determining at least one of a current position and a current orientation of at least one of the device interface 12 and a device (e.g., guidance device 14 or a surgical tool accommodated therein) received by the device interface 12. Determining the current position and/or orientation may be performed using a surgical navigation system tracking the tracking device 20 within a given coordinate system. As described with reference to FIG. 2A, a positional relationship between the tracking device 20 and the guidance device 14 of the surgical arm 10 may be known a priori (e.g., because it is fixed). In an operating state of the surgical arm 10, the guidance device 14 will be coupled to the device interface 12. As such, the tracking device 20 will be in a fixed spatial relationship to the device interface 12 and the guidance device 14 received therein (and, of course, in a fixed spatial orientation to a surgical tool guided by the guidance device 14). Thus, in the embodiment of FIG. 2A, the current position and orientation of the first interface 12 and the guidance device 14 can easily be tracked by the surgical navigation system.

The method continues in step S02 with determining at least one of a target position and a target orientation of the device interface 12 or the guidance device 14. The target position and/or orientation will be determined based on the pre-determined surgical approach. As an example, the target position and target orientation of the device interface 12 or the guidance device 14 may be defined to be concentrically aligned with a linear trajectory connecting the planned or actual entry point (e.g., in the patient's skull) with the surgical target (e.g., a brain tumor).

If a difference between the current and target positions and/or current and target orientations is detected (e.g., by the surgical navigation system), it is determined in step S03 that an adjustment of the surgical arm 10 is required relative to at least one adjustment axis (e.g., adjustment axis 30, 32 or 34). The difference may for example be given by a distance (e.g., in millimeters) by which a position of the surgical arm 10 deviates in a certain direction from the pre-determined surgical approach. Alternatively or additionally, the difference may also be given by an angle (e.g., in degrees) by which an orientation of the surgical arm 10 deviates from the pre-determined surgical approach.

If an adjustment according to step S03 is required, the navigation system (e.g., a processing unit thereof) triggers the display of visual guidance for a user in order to properly adjust a position and/or orientation of the surgical arm 10 in accordance with the pre-determined surgical approach. Visual guidance may be provided by displaying on a display device a visual coding associated with the at least one operating member 36, 38, 40, 42 that is associated with the at least one adjustment axis 30, 32, 34 relative to which the surgical arm 10 deviates from the pre-determined surgical approach.

The provision of visual guidance will be explained in the following in more detail with reference to FIGS. 5 and 6A to 6D.

Figure 5:
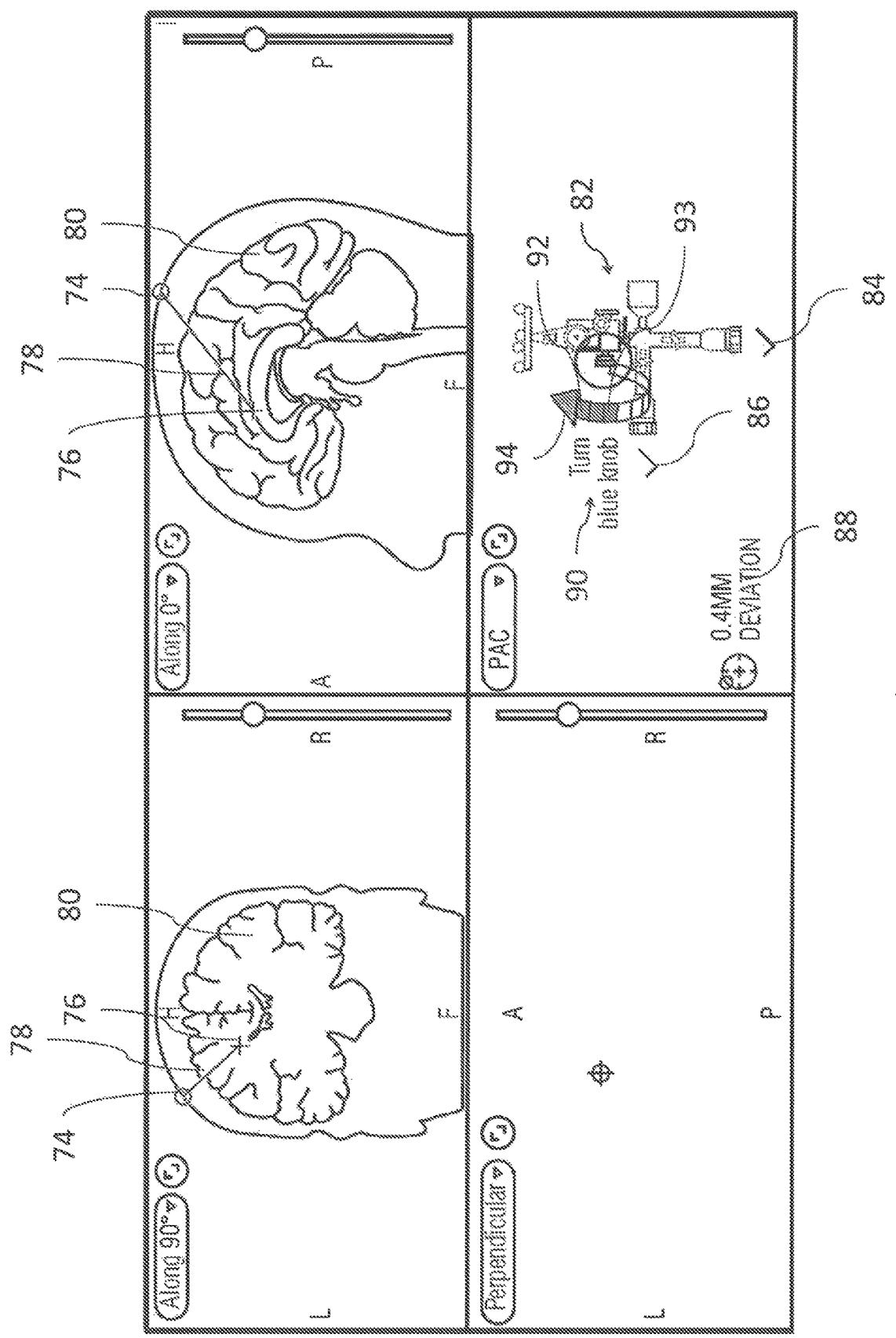
FIG. 5 shows different representations of visual guidance for operating a surgical arm according to a pre-determined surgical approach.

FIG. 5 shows an exemplary display of a display device, such as a monitor of the surgical navigation system. The display provides visual guidance for operating the surgical arm 10 according to the pre-determined surgical approach and based on the visually coded operating members 36, 38, 40 and 42.

In FIG. 5, a pre-determined surgical approach for reaching a brain tumor is depicted. A planned entry point on a patient's skull is indicated by a circle 74 and a planned target location defined by the tumor is indicated by a cross 76. The corresponding surgical approach defines a planned trajectory of a surgical tool (e.g. a biopsy needle). This trajectory is represented by a straight line 78 connecting the entry point 74 and the target location 76.

In FIG. 5, three different views of the pre-determined surgical approach are shown relative to a pre-operative or intra-operative image of the patient's skull. In the top left view of the exemplary display of FIG. 5, a cross-sectional front view of the patient's skull is displayed together with a view of the patient's brain 80 and the pre-determined surgical approach 74, 76, 78. In the top right view of the exemplary display of FIG. 5, a cross-sectional side view of the patient's skull is shown together with a view of the brain 80 and the pre-determined surgical approach 74, 76, 78. In other words, the view according to the top right illustration is rotated by 90° with respect to the view according to the top left illustration. In the bottom left illustration of the exemplary display of FIG. 5, a view perpendicular to the pre-determined surgical approach 74, 76, 78 is shown, i.e., the actual view a surgeon would see before entering a surgical instrument inside the patient's skull. The images of the patient's skull and brain 80 in the top row of the exemplary display of FIG. 5 may be obtained by 3D Computer Tomography (CT) imaging or using Magnetic Resonance Imaging (MRI).

In the bottom right view of FIG. 5, visual guidance for operating the surgical arm 10 according to the pre-determined surgical approach is provided. In more detail, a schematic representation 82 of the surgical arm 10 is shown. The schematic representation 82 of the surgical arm 10 is further accompanied by checkmarks 84, 86. Each of the checkmark 84, 86 is associated with a dedicated movement relative to one of the adjustment axes 30, 32, 34 by operating one of the four operating members 36, 38, 40, 42 and indicates that the surgical arm 10 is already aligned with respect to at least one of the adjustment axes 30, 32, 34 and the planned surgical trajectory 78 (for adjustment axis 30, only the translational movement is completed, whereas a rotational movement is still needed for proper alignment).

Further, the computer system provides the user with information regarding a specific operating member 36, 38, 40 and 42 associated with a specific adjustment axis 30, 32, 34 to be operated for proper alignment of the surgical arm 10 (i.e., of the device interface 12 and/or the guidance device 14) according to the pre-determined surgical approach. In the embodiment of FIG. 5, the user is provided with visual information relating to the operating member 40 that is associated with the adjustment axis 30. The information comprises a numerical value 88 indicative of an amount by which the alignment of the surgical arm 10 deviates from the pre-determined surgical approach 74, 76, 78 relative to the adjustment axis 34.

The deviation of the alignment of the surgical arm 10 from the pre-determined surgical approach relative to each of the adjustment axes 30, 32, 34 may exemplarily be calculated as follows. The pre-determined surgical approach 74, 76, 78 may be planned and registered in the coordinate system of a surgical navigation system, e.g., based on image data of a surgical imaging method such as CT or MRI.

Further, the position of the tracking device 20 received in the second interface 18 may be tracked by a tracking component of the surgical navigation system, such as a camera. As the tracking device 20 is arranged in a known spatial relationship to a surgical tool received in the first interface 12, the position and/or orientation of the surgical tool (i.e., the actual trajectory of the tool) may be derived based on the known spatial relationship. Said position and/or orientation of the surgical tool may then also be registered into the coordinate system of the surgical navigation system. The angles between the pre-determined surgical approach 74, 76, 78 and the position and/or orientation of the surgical tool received in the first interface 12 may then be calculated in at least two dimensions, based on the above determinations. As such, the angular distances between the pre-determined surgical approach 74, 76, 78 and the actual trajectory of the surgical tool may be known with respect to every adjustment axis 30, 32, 34.

Further, the visual information comprises an indication of which of the operating members 36, 38, 40 and 42 a user has to turn in order to compensate the misalignment associated with the numerical value 88. In the embodiment of FIG. 5, the operating members 36, 38, 40 and 42 are not visually coded with geometric patterns as in FIGS. 1 to 3C, but are visually coded with different colors. It will be appreciated that both types of visual codings are interchangeable and can also be combined. In the present case, operating member 40 is marked with a blue color and configured as a turning knob (see FIG. 1). Therefore, a user is informed by a text message that the blue knob is to be turned (see reference numeral 90). Visual guidance in regard to an amount 92 by which the operating member 40 is to be turned and a direction 94 in which the operating member 40 is to be turned is further provided to the user. In the embodiment of FIG. 5, the amount 92 by which the operating member 40 is to be turned is represented by a number of color-coded rectangles 93. The rectangles 93 are coded with the same color as the respective turning knob 40 (i.e., blue). A direction 94 in which the turning knob 40 is to be turned is represented by an arrow, indicating a counterclockwise rotation in the embodiment of FIG. 5. It is to be understood that the above-described visual guidance only serves illustrative purposes and is in no way intended to limit the scope of the present disclosure.

The visual guidance regarding a specific operating member associated with a specific adjustment axis as provided to a user will now be described in more detail with respect to FIGS. 6A to 6D. In particular, an exemplary alignment process of the surgical arm 10 relative to the adjustment axis 30 (rotatory alignment) associated with the operating member 40 is shown in several steps indicative of a temporal sequence. It will be apparent that similar guidance will be provided for a translator alignment in regard to the axis 30 and for alignment relative to the remaining axes 32, 34, but using other colors (e.g., red, yellow and green).

Figure 6A:
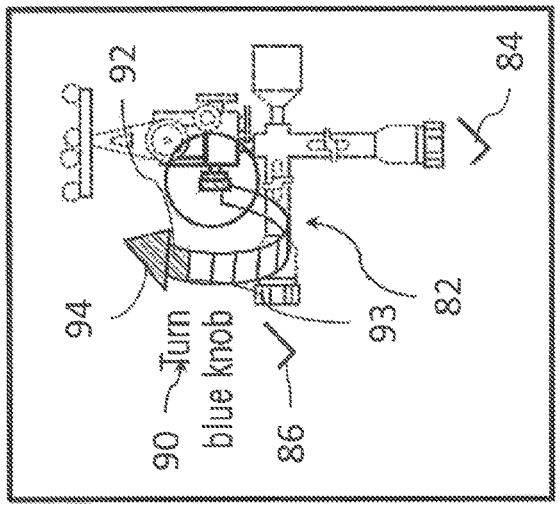
FIGS. 6A-6D show a temporal sequence of visual guidance based on a visual coding and in combination with an indication of a direction in which an associated operating member is to be operated.

FIG. 6A shows the beginning of the alignment process of the surgical arm 10 around adjustment axis 30. As already shown in the bottom right view of FIG. 5, the user is provided with the schematic representation 82 of the surgical arm 10, as well as the checkmarks 84, 86 indicating that the surgical arm 10 is already aligned with respect to translational movements along adjustment axes 30 and 32. Additionally, the user is also provided with visual guidance 90 as to the operating member that is to be turned, visual guidance 92 as to the amount by which the operating member is to be turned, and visual guidance 94 as to the direction the operating member is to be turned. Specifically, the visual guidance 92 as to the amount the operating member is to be turned is represented by a number of color-coded rectangles 93. In FIG. 6A, three color-coded rectangles 93 are displayed. This display indicates that the operating member marked in blue is to be turned in the direction indicated by arrow 94 (i.e., in counterclockwise direction) by four entire turns (three color-coded rectangles 93 and the color-coded head of arrow 94). Alternatively, the number of color-coded rectangles 93 may indicate a specific amount of degrees (e.g., in steps of 10° or more) by which a particular operating member is to be turned. For example, one color-coded rectangle 93 may be indicative of turning the blue operating member by 90° in the direction indicated by arrow 94. Alternatively, one color-coded rectangle 93 may be indicative of turning the blue operating member by 10° in the direction indicated by arrow 94. In the case where the color-coded rectangles 93 are indicative of an amount of degrees by which the operating members are to be turned, a user may be informed (e.g., haptically) if the operating member has been turned by the specified amount of degrees. For example, the user may be informed that the blue operating member has been rotated 90° in a counterclockwise direction by providing a small mechanical resistance every 90°. Thus, the user may need to apply a slightly greater force to overcome the mechanical resistance in order to rotate the turning knob further.

The required number of turns by which a specific operating member is to be turned may exemplarily be calculated as follows. Each of the operating members 36, 38, 40 and 42 may be provided with a thread member for operating the respective adjustment member 22, 24, 26 and 28. The thread members may have known thread pitches. For example, the operating members 36 and 38 configured to operate the adjustment members 22 and 24, respectively, may be turning knobs and may have a pitch of 2 mm. Turning the turning knobs 36 or 38 for an entire turn (i.e., 360°) may thus for example cause the biopsy arm 10—and hence also a surgical tool received inside the first interface 14—to move along the respective adjustment axes 30 or 32 by 2 mm. Depending on the dimensions of the mechanical components of the surgical arm 10, moving the surgical arm 10 by 2 mm along an adjustment axis may correspond to a rotation of the surgical tool by 2.25°. In a further example, the operating members 40 and 42 configured to operate the adjustment members 26 and 28, respectively, may also be turning knobs and may have a pitch of 0.75 mm. Turning the turning knobs 40 or 42 for an entire turn (i.e., 360° may thus for example cause the biopsy arm 10—and hence also a surgical tool received inside the first interface 14—to rotate around the respective adjustment axes 30 or 34 by 1.75°, depending on the dimensions of the mechanical components of the surgical arm 10. These known relations between an amount of turns of the operating members 36, 38, 40 and 42 configured as turning knobs and a rotation of the surgical tool relative to a specific adjustment axis 30, 32 and 34 may be transformed by the computer system into the visual guidance 92 as to the amount a respective operating member is to be turned.

Figure 6B:
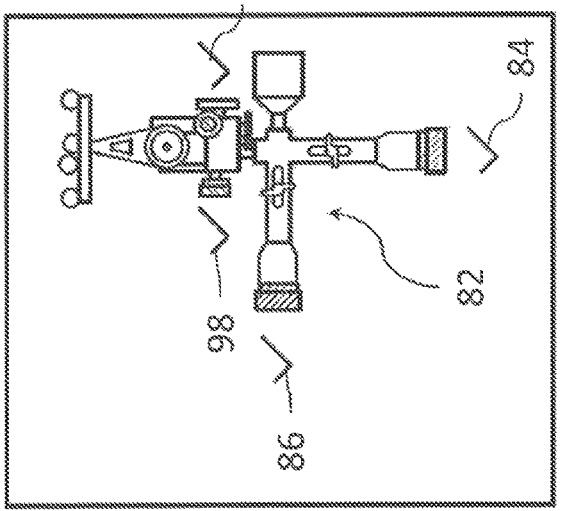

FIG. 6B shows a first intermediate state of the alignment process of the surgical arm 10 around adjustment axis 30 according to a pre-determined surgical approach. As illustrated in FIG. 6B, the blue operating member has already been rotated by an amount corresponding to two color-coded rectangles 93. For example, the blue operating member has been rotated by two entire turns or alternatively has been rotated by 180°, or alternatively has been rotated by 20°.

Figure 6C:
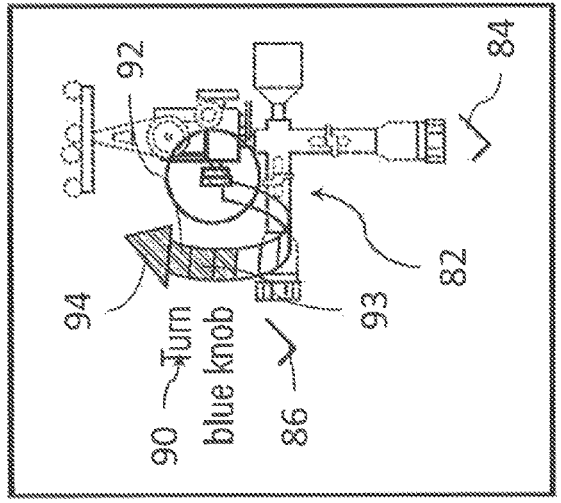

FIG. 6C shows a later intermediate state of the alignment process of the surgical arm 10 around adjustment axis 30. Here, the blue operating member has already been rotated by an amount corresponding to three color-coded rectangles 93. For example, the blue operating member has been rotated by three entire turns or alternatively has been rotated by 270°, or alternatively has been rotated by 30°.

Figure 6D:
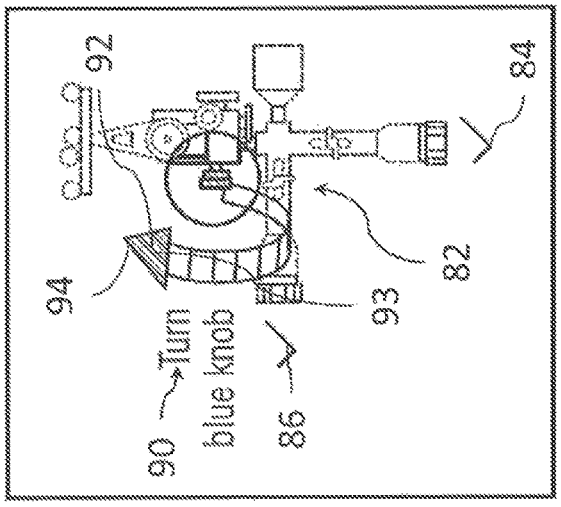

FIG. 6D shows the final state of the alignment process of the surgical arm 10 around the adjustment axis 30. Here, the surgical arm 10 is properly aligned in accordance with the pre-determined surgical approach with respect to all possible movements relative to all adjustment axes 30, 32, 34. Therefore, each of the corresponding operating members 36, 38, 40 and 42 associated with the respective adjustment axes 30, 32 and 34 is provided with a checkmark 84, 86, 96, 98. Hence, when all operating members 36, 38, 40 and 42 are provided with checkmarks as depicted in FIG. 6D, the user may conclude that the alignment process of the surgical arm 10 according to the pre-determined surgical approach has ended. In the next step, a surgical procedure may now be performed.

When the adjustment process is completed for a dedicated movement relative to a particular adjustment axis, i.e., when one of the checkmarks 84, 86, 96, 98 is displayed, the user will secure this adjustment by operating the associated locking member 52, 54, 56, 58. In some variants, a text message is displayed in this case to explicitly request the user to do so.

In the above embodiments, a surgical arm 10 comprising visually coded operating members 36, 38, 40 and 42 as well as a method of providing visual guidance for operating the surgical arm 10 have been presented. As has become apparent from the embodiments, the visual coding of the operating members 36, 38, 40, 42 facilitates the identification of a specific operating member 36, 38, 40, 42 by a user. Therefore, the alignment process of the surgical arm 10 can be made faster upon providing proper visual guidance.

In some variants, locking members 52, 54, 56, 58 are associated with the operating members 36, 38, 40 and 42 and are coded with the same visual coding as the associated operating member 36, 38, 40 and 42. Hence, the user easily identifies a specific locking member 52, 54, 56, 58 associated with the operating member 36, 38, 40, 42 the user is currently operating or wishes to operate next. This further speeds up the alignment process and at the same time increases user convenience. Moreover, as the association between an individual operating member 36, 38, 40, 42 and the respective locking member 52, 54, 56, 58 is immediately apparent to the user due to the same visual coding, the risk that the user operates a wrong operating member 36, 38, 40, 42 and/or locking member 52, 54, 56, 58 such that the surgical arm 10 is not correctly aligned (e.g., brought out of previously established alignment) is reduced.

Additionally, the different visual codings of the operating members 36, 38, 40, 42 are also perceivable and distinguishable by an electronic component, e.g., a camera. As such, a computer system attached to the camera (e.g., a surgical navigation system) can easily determine the specific operating member 36, 38, 40, 42 that is currently operated and which operating member 36, 38, 40, 42 should be operated next according to a pre-determined surgical approach. The computer system can transfer this information to a user aligning the surgical arm 10 in an easy and definite way by simply providing the user with the respective visual coding of said operating member 36, 38, 40, 42. Thus, there is no need for the user to first transform (possibly erroneously) the information received from the computer system into corresponding operation steps. Consequently, user convenience is further improved and at the same time the failure rate in the alignment process of the surgical arm 10 is lowered.

The invention claimed is:

1. A method of providing visual guidance for operating a surgical arm according to a pre-determined surgical approach, the surgical arm comprising a first interface configured to receive a device for performing or assisting a surgical procedure, multiple adjustment members configured to adjust the surgical arm relative to different adjustment axes, and at least two operating members configured to operate different ones of the adjustment members, wherein the operating members are marked with different visual codings, the method comprising the steps of:

determining at least one of a current position and a current orientation of the first interface or a device received by the first interface;

determining, based on the pre-determined surgical approach, at least one of a target position and a target orientation of the interface or the device;

based on a difference between at least one of the current and target positions and the current and target orientations, determining that an adjustment of the surgical arm is required relative to at least one of the adjustment axes; and triggering a display of the visual coding associated with one of the at least two operating members that is associated with the at least one adjustment axis so as to provide visual guidance, wherein the visual guidance comprises the display of the visual coding in combination with an indication of an amount by which the associated operating member is to be operated.

2. The method according to claim 1, wherein the visual guidance comprises a display of the visual coding in combination with an indication of a direction in which the associated operating member is to be operated.

3. The method according to claim 1, wherein the indication of an amount by which the associated operating member is to be operated is in a form of at least one of a first number of geometric elements and a first geometric form in association with the visual coding of the operating member.

4. The method according to claim 3, further comprising displaying at least one of a second number of geometric elements and a second geometric form in association with a visual coding different than the visual coding of the first number of geometric elements and the first geometric form, respectively, the second number of geometric elements or the second geometric form being indicative of an amount by which the associated operating member has been operated.

5. The method according to claim 1, further comprising:
determining a specific adjustment axis relative to which the surgical arm deviates the most among all adjustment axes from the pre-determined surgical approach; and
prioritizing the provision of visual guidance for said specific adjustment axis over any other adjustment axis.

6. The method according to claim 1, further comprising triggering a display of a numerical value indicative of an amount by which a specific adjustment axis deviates from the pre-determined surgical approach.

7. The method according to claim 1, further comprising triggering a display of a superposition of at least one of the current position and the current orientation of the first interface or a device received in the first interface relative to the pre-determined surgical approach.

8. The method according to claim 1, wherein the at least one of a current position and a current orientation of the first interface or the device received by the first interface is determined by tracking, using a surgical navigation system, a tracking device that is in a fixed spatial relationship with at least one of the first interface and the device received by the first interface.

9. A system comprising:
a surgical arm comprising:
a first interface configured to receive a device for performing or assisting a surgical procedure;
multiple adjustment members configured to adjust the surgical arm relative to different adjustment axes; and
at least two operating members configured to operate different ones of the adjustment members, wherein the operating members are marked with different visual codings; and
a computer program product comprising computer program instructions configured to be executed by a processor to cause the processor to perform a method of providing visual guidance for operating the surgical arm according to a pre-determined surgical approach in which the processor is configured to:
determine at least one of a current position and a current orientation of the first interface or a device received by the first interface;
determine, based on the pre-determined surgical approach, at least one of a target position and a target orientation of the interface or the device;
based on a difference between at least one of the current and target positions and the current and target orientations, determining that an adjustment of the surgical arm is required relative to at least one of the adjustment axes; and
trigger displaying the visual coding associated with one of the at least two operating members that is associated with the at least one adjustment axis so as to provide visual guidance,
wherein the visual guidance comprises the displaying of the visual coding in combination with an indication of an amount by which the associated operating member is to be operated.

10. The system according to claim 9, wherein the visual guidance comprises a display of the visual coding in combination with an indication of a direction in which the associated operating member is to be operated.

11. The system according to claim 10, wherein the at least one of a current position and a current orientation of the first interface or the device received by the first interface is determined by tracking, using a surgical navigation system, a tracking device that is in a fixed spatial relationship with at least one of the first interface and the device received by the first interface.

12. The system according to claim 9, wherein the indication of an amount by which the associated operating member is to be operated is in a form of at least one of a first number of geometric elements and a first geometric form in association with the visual coding of the operating member.

13. The system according to claim 12, wherein the processor is further configured to trigger displaying of at least one of a second number of geometric elements and a second geometric form in association with a visual coding different than the visual coding of the first number of geometric elements and the first geometric form, respectively, the second number of geometric elements or the second geometric form being indicative of an amount by which the associated operating member has been operated.

14. The system according to claim 9, wherein the processor is further configured to:
determine a specific adjustment axis relative to which the surgical arm deviates the most among all adjustment axes from the pre-determined surgical approach; and
prioritize the provision of visual guidance for said specific adjustment axis over any other adjustment axis.

15. The system according to claim 9, wherein the processor is further configured to trigger displaying of a numerical value indicative of an amount by which a specific adjustment axis deviates from the pre-determined surgical approach.

16. The system according to claim 9, wherein the processor is further configured to trigger displaying of a superposition of at least one of the current position and the current orientation of the first interface or a device received in the first interface relative to the pre-determined surgical approach.

17. A computer program product comprising a non-transitory computer-readable storage medium storing computer program instructions, which when executed on a processor, are configured to cause the processor to perform the steps of:
    determining at least one of a current position and a current orientation of a first interface or a device received by the first interface;
    determining, based on a pre-determined surgical approach, at least one of a target position and a target orientation of the first interface or the device;
    based on a difference between at least one of the current and target positions and the current and target orientations, determining that an adjustment of a surgical arm is required relative to at least one adjustment axis; and
    triggering a display of a visual coding associated with at least one operating member associated with the at least one adjustment axis so as to provide visual guidance,
    wherein the visual guidance comprises the display of the visual coding in combination with an indication of an amount by which the associated operating member is to be operated.

18. The computer program product according to claim 17, wherein the visual guidance comprises a display of the visual coding in combination with an indication of a direction in which the associated operating member is to be operated.

19. The computer program product according to claim 18, wherein the indication of an amount by which the associated operating member is to be operated is in a form of at least one of a first number of geometric elements and a first geometric form in association with the visual coding of the operating member.

20. The computer program product according to claim 19, wherein the computer program instructions upon execution are further configured to cause the processor to trigger displaying at least one of a second number of geometric elements and a second geometric form in association with a visual coding different than the visual coding of the first number of geometric elements and the first geometric form, respectively, the second number of geometric elements or the second geometric form being indicative of an amount by which the associated operating member has been operated.

* * * * *